US010850000B2

(12) United States Patent
Lewis

(10) Patent No.: US 10,850,000 B2
(45) Date of Patent: Dec. 1, 2020

(54) MIST GENERATOR FOR STERILIZING FORCED HOT AIR INTRAOPERATIVE PATIENT WARMER WITH IMPROVED STERILITY

(71) Applicant: Randall J. Lewis, Bethesda, MD (US)

(72) Inventor: Randall J. Lewis, Bethesda, MD (US)

( * ) Notice: Subject to any disclaimer, the term of this patent is extended or adjusted under 35 U.S.C. 154(b) by 539 days.

(21) Appl. No.: 15/722,822

(22) Filed: Oct. 2, 2017

(65) Prior Publication Data

US 2018/0028702 A1 Feb. 1, 2018

Related U.S. Application Data

(63) Continuation-in-part of application No. 15/334,507, filed on Oct. 26, 2016, now Pat. No. 9,901,483, which is a continuation-in-part of application No. 15/056,120, filed on Feb. 29, 2016, now Pat. No. 9,504,601.

(51) Int. Cl.
| | |
|---|---|
| *A61L 2/16* | (2006.01) |
| *A61L 2/22* | (2006.01) |
| *A61F 7/00* | (2006.01) |
| *A61L 2/26* | (2006.01) |

(Continued)

(52) U.S. Cl.
CPC .............. *A61L 2/22* (2013.01); *A61F 7/0085* (2013.01); *A61F 7/0097* (2013.01); *A61L 2/26* (2013.01); *B01D 46/00* (2013.01); *A61F 2007/0055* (2013.01); *A61F 2007/0094* (2013.01); *A61L 9/16* (2013.01); *A61L 2202/122* (2013.01); *A61L 2202/123* (2013.01); *A61L 2202/15* (2013.01); *A61L 2202/24* (2013.01); *A61L 2209/14* (2013.01)

(58) Field of Classification Search
CPC ..... A61L 2/22; A61L 2/26; A61L 9/16; A61L 2209/14; A61L 2202/123; A61L 2202/122; A61L 2202/15; A61L 2202/24; B01D 46/00; A61F 7/0085; A61F 7/0097; A61F 2007/0094; A61F 2007/0055
See application file for complete search history.

(56) References Cited

U.S. PATENT DOCUMENTS

| | | | | |
|---|---|---|---|---|
| 1,121,227 A | 12/1914 | Mitchell | ........................ | 156/533 |
| 2,259,712 A | 10/1941 | Sweetland | ........................ | 5/421 |

(Continued)

*Primary Examiner* — Kaitlyn E Smith
*Assistant Examiner* — Yasamin Ekrami
(74) *Attorney, Agent, or Firm* — Ernest D. Buff & Associates, LLC; Ernest D. Buff; Margaret A. LaCroix

(57) ABSTRACT

A mist generator improves sterility of blowers having controlled forced air for patient warmers and lifters. The mist generator has a main body including a top wall with an opening, that traverses into a chamber adapted to receive a disinfectant, side walls and a bottom wall. The main body further includes an inlet duct adapted for attachment to a first hose which, in turn, is adapted for attachment to an output opening of the blower for delivery into the chamber of forced air carrying misted disinfectant. The main body also includes an output duct adapted for attachment to a second hose which, in turn, is adapted for attachment to an inlet opening of the blower for delivery of disinfectant misted air through internal components of the blower. The mist generator improves sterility of the blower, thereby mitigating microbial contamination of patient warmers and lifters, and hospital environments.

19 Claims, 11 Drawing Sheets

(51) Int. Cl.
  *B01D 46/00* (2006.01)
  *A61L 9/16* (2006.01)

(56) References Cited

U.S. PATENT DOCUMENTS

| | | | | |
|---|---|---|---|---|
| 2,504,308 | A | | 4/1950 | Donkle .......................... 62/261 |
| 2,706,702 | A | * | 4/1955 | Carski .................... C12M 23/08 |
| | | | | 435/252.1 |
| 2,753,435 | A | | 7/1956 | Jepson ......................... 126/204 |
| 2,978,225 | A | | 4/1961 | Dallas ............................ 165/46 |
| 4,094,357 | A | | 6/1978 | Sgroi ...................... 165/104.26 |
| 4,132,262 | A | | 1/1979 | Wibell ......................... 165/206 |
| 4,777,802 | A | | 10/1988 | Feher ............................. 62/3.3 |
| 4,884,304 | A | | 12/1989 | Elkins ............................. 5/421 |
| 5,318,568 | A | * | 6/1994 | Kaufmann ................ A61F 7/00 |
| | | | | 285/320 |
| 5,902,413 | A | | 5/1999 | Puszko ......................... 134/21 |
| 5,968,084 | A | | 10/1999 | Augustine et al. ........... 607/107 |
| 7,114,204 | B2 | | 10/2006 | Patrick ........................ 5/81.1 R |
| 7,658,891 | B1 | * | 2/2010 | Barnes .................... A61L 9/015 |
| | | | | 128/205.28 |
| 7,837,721 | B2 | | 11/2010 | Augustine et al. ............. 607/96 |
| 8,414,671 | B2 | | 4/2013 | Augustine et al. .......... 55/358.2 |
| 9,010,953 | B1 | * | 4/2015 | Wells ..................... B65D 43/02 |
| | | | | 362/101 |
| 2002/0058974 | A1 | | 5/2002 | Van Duren ..................... 607/96 |
| 2003/0208251 | A1 | | 11/2003 | Papay .......................... 607/107 |
| 2003/0216660 | A1 | | 11/2003 | Ben-Oren ..................... 600/532 |
| 2010/0234794 | A1 | | 9/2010 | Weadock ....................... 604/20 |
| 2011/0315893 | A1 | * | 12/2011 | Pugh ......................... G02C 7/04 |
| | | | | 250/455.11 |
| 2015/0129439 | A1 | | 5/2015 | Friesen ......................... 206/222 |
| 2015/0182650 | A1 | * | 7/2015 | Leight ........................ A61L 2/24 |
| | | | | 422/292 |

\* cited by examiner

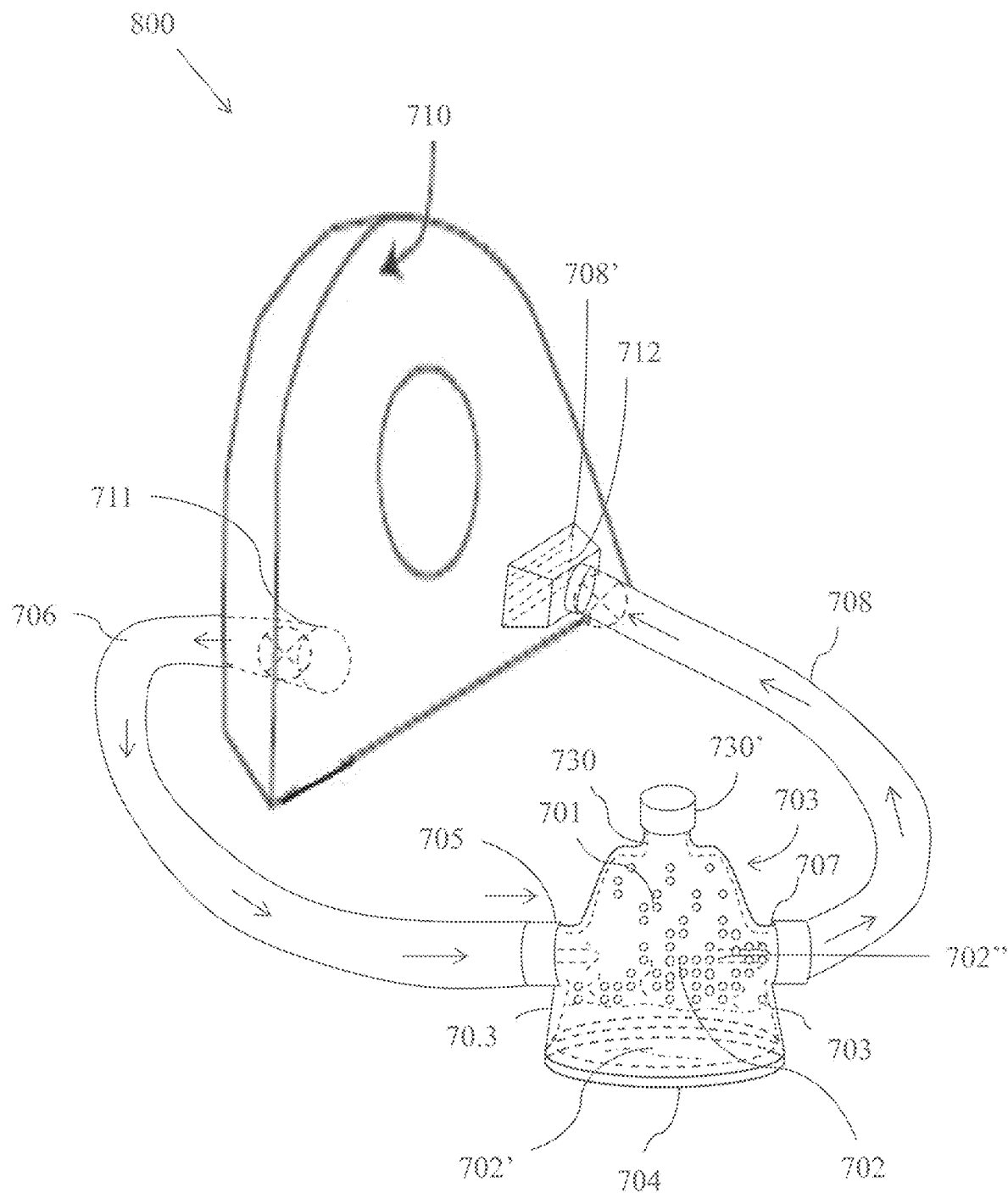

MIST GENERATOR FOR STERILIZING FORCED HOT AIR INTRAOPERATIVE PATIENT WARMER WITH IMPROVED STERILITY

CROSS-REFERENCE TO RELATED APPLICATIONS

This application is a continuation-in-part of applicant's U.S. patent application Ser. No. 15/334,507, filed Oct. 26, 2016, now U.S. Pat. No. 9,901,483, which is a continuation in part of U.S. patent application Ser. No. 15/056,120, filed Feb. 29, 2016, now U.S. Pat. No. 9,504,601, the disclosures of which are hereby incorporated in their entirety by reference thereto.

1. Field of the Invention

The present invention relates to improvements in sterility of intraoperative patient warmers, such as blowers for thermal blankets and/or mattresses; and, more particularly, to an antimicrobial mist generator for systems employing forced heated air within a thermal blanket or mattress, warming the patient and preventing hypothermia, while maintaining the sterility of the operative area on the patient.

2. Description of the Prior Art

Numerous prior art patents and disclosures relate to warming of a patient mattress or blanket by the passage of warmed fluids. Warmed fluids may be heated water or heated air. If a fluid-filled device leaks or ruptures, the heated water disadvantageously creates puddles of leaked water around the patient and on the operating room floor. Water filled blankets are heavy and the patient may find these blankets highly uncomfortable. Mattresses and blankets that circulate warm air discharge the air through a plurality of exit passages in the form of high velocity jets. The discharge creates turbulent circulation currents in the room air that may pick up microbes in floor dust and deliver them to the patient's operative area, as well as hospital room workers.

U.S. Pat. No. 1,121,277 to Mitchell discloses a warming appliance for beds. This warming apparatus circulates warm water. The disclosure of this patent shows the bed having a plurality of pipes through which heated water is circulated. A hot water heater or boiler is connected to a pipe that feeds the bed heating pipes. Warm air is not circulated through the bed.

U.S. Pat. No. 2,259,712 to Sweetland discloses a bed warmer apparatus. A fan blows air through an electric heater and the warmed air is passed through a pipe in the bed. The bed warmer requires power to drive the blower motor. A flexible hose conveys warm air to the cushion, which serves the double purpose of supporting the bed cover and providing warmth in the bed. A conventional type of bed cover is used. The blower passes air over electrical heaters to warm the air, which is passed through pipes in the bed. The interior of the blower is not sterilized. The warm air is not returned to the blower since this is not a closed system. Release of the warm air can cause currents of unsterile air, containing bacteria, to surround the patient or the operative site, increasing prospects for infections.

U.S. Pat. No. 2,504,308 to Donkle discloses a heating and cooling cover. The bed has a heating or cooling cover supplied with a working fluid from a refrigerator or a heat pump. The cover does not employ warm air. A working fluid is returned to the refrigeration or heat pump system through a heat exchanger, which heats or cools the area adjacent to the refrigeration or heat pump unit.

U.S. Pat. No. 2,753,435 to Jepson discloses a thermal blanket. The thermal blanket is on a bed and is provided with a fluid circulating unit. The fluid circulating unit is provided with a knob to adjust the temperature of the thermal blanket. The fluid is indicated to be distilled water. The device disclosed by the Jepson patent does not circulate warm air within the blanket.

U.S. Pat. No. 2,978,225 to Dallas discloses a thermal blanket. The thermal blanket is provided with tubes through which liquid is circulated. The thermal blanket has a plurality of fluid passage ways disposed in a parallel relationship. The edge includes a liquid distribution manifold unit. The thermal blanket does not circulate warm air to provide warmth to the patient.

U.S. Pat. No. 4,094,357 to Sgroi discloses a heat transfer blanket. The heat transfer blanket has a plurality of flexible sheath heat pipes that provide a uniform heating or cooling pattern therein. The ends of the flexible heat pipes that are free from the blanket are thermally coupled to a combination heating and cooling system. When utilizing the heating system, the flexible heat pipes provide elevated temperatures at the blanket surfaces. When utilizing the cooling system, the flexible heat pipes provide lower than ambient temperatures at the blanket surfaces. A solid metallic rod is affixed to one end of the pipe. A wick extends the entire length of the interior of the pipe, which is partially filled with a liquid that becomes a vapor upon sufficient heating. The end of the pipe in which liquid is situated accepts heat from the surrounding area, causing the liquid to vaporize. The vapor ultimately communicates with the other end of the pipe. At this end, cooling effects are introduced and the vapor condenses back to a liquid state. Liquid then travels along the wick to the end of a tube containing the liquid. The efficiency of thermal coupling between opposite ends of the heat pipe is substantially higher than the coupling efficiency of an equivalent diameter and length of a solid copper rod. The heat transfer means for warming or cooling the blanket is by evaporation heating or cooling of liquid contained in the wick. Warm air is not passed within pipes in the heat transfer blanket.

U.S. Pat. No. 4,132,262 to Wibell discloses a heating and cooling blanket. This cooling and heating blanket has a blanket enclosure with heating means including a plurality of flexible elements positioned within the enclosure for being electrically energized to supply heat to the enclosure so that the enclosure may be retained above room temperature. A cooling means includes a plurality of flexible fluid carrying conduits positioned within the enclosure through which a heat transfer fluid can flow, such that the enclosure may be retained below room temperature. Control means including an electric motor and a pump driven thereby are located remotely relative to the enclosure. A flexible conduit means connects the enclosure and the cooling means. A regulating means is operatively associated with the heating means and the cooling means. The regulating means is adapted to energize the control means or the heating means in response to increases and decreases of the temperature associated with the enclosure. With this arrangement, the temperature of the blanket may be retained above or below the room temperature in which the blanket is located. The heating and cooling means are separate from each other. The heating means comprises electrical heating wires, which are heated by the passage of an electrical current. Heating of the blanket is not achieved by the passage of warm air.

U.S. Pat. No. 4,777,802 to Feher discloses a blanket assembly and selectively adjustable apparatus for providing heated or cooled air thereto. This blanket assembly has an outer layer constructed of a relatively close weave fabric preventing air flow there through. Underneath the top layer is a second layer of material edge connected to the top layer and which is constructed of a material permeable to air, such as relatively thin taffeta, for example. A cavity between the two layers receives pressurized cooled or heated air that passes through the air permeable layer to cool or heat the individual using the blanket assembly. A modified blanket assembly construction includes rigid edge wall members holding the outer and inner layers separated at a predetermined spacing. This reduces "pinch-off" between the layers that would restrict airflow within parts of the cavity or chamber. Peltier effect elements are selectively energizable to heat or cool air provided to the blanket assembly cavity. The heating/cooling of the patient bed is effected by a closed circuit with a solid state PN junction to create the heating/cooling based on the Peltier effect. Passage of direct current in one direction causes one PN junction to heat while the other junction cools. The heated PN junction supplies heat to warm the patient bed while the coolness of the other junction is discharged in air surrounding the patient as well as the operating room. The device disclosed by the Feher patent does not use circulation of warm air in a closed system to warm the bed of a patient and there is no sterilization of the internal portion of the system, creating the possibility of infecting the patient and workers in the operating room.

U.S. Pat. No. 4,884,304 to Elkins discloses a bedding system with selective heating and cooling. This bedding system has provision for heating or cooling a person and for applying the heating or cooling only in areas of the bed where the person is located. A sealed three-ply heat transfer and insulating device covers the mattress, below the contour sheet or other covering which comes in contact with the person's body. A wicking contour sheet or other cover capable of absorbing any condensation on the surface of the three-ply device may optionally be used. Between the lower two plies of the three-ply material is channeled a flow of coolant liquid at a regulated temperature that are close to human skin temperature. Above these two plies. i.e. between the middle ply and the upper ply, is a sealed envelope containing slightly pressurized air. A light weight, well-insulated comforter is also recommended to isolate the sleeper from the thermal ambient environment. The bedding system includes a temperature control unit and a mattress cover device, which is positioned over a mattress. The mattress cover device includes liquid flow channels and preferably a gas envelope or plenum space located above the liquid flow channels. The multiplicity of liquid flow channels is interconnected to form one or more circulation paths. The mattress is heated by liquid flow channels. It is not heated by the passage of warm air.

U.S. Pat. No. 5,968,084 to Augustine et al. discloses a thermal blanket. This thermal blanket includes an inflatable covering with a head end, a foot end, two edges and an undersurface. The covering is inflated through an inlet at the foot end by a thermally-controlled inflating medium. An aperture array on the undersurface of the covering exhausts the thermally controlled inflating medium from the covering. Exhaust port openings are provided at the edges of the covering to vent the inflating medium, which enhances circulation of the thermally-controlled medium through the cover. An uninflatable section is provided at the head end, together with an absorbent bib attached to the covering, adjacent the uninflatable section. An uninflatable section may also be provided at the foot end having a pair of seams to form an erectable drape section. When inflated, the device self-erects and provides a bath of thermally-controlled inflating medium to the interior of the erected structure. The enhanced circulation of the medium through the covers maintains a relatively high average temperature under the blanket and a relatively uniform distribution of temperature in the inflating medium which is exhausted through the apertures into the structure's interior. When the structure covers a patient, the uninflatable section at the head end provides a relatively unobstructed view of the patient's face, while the absorbent bib maintains a relatively sanitary environment in the area beneath the patient's head. The uninflatable section at the foot end retains heat from the inflating medium to warm the patient's feet and insulate the bare skin of the feet from excessive conductive heat from the hose connected to the inflation inlet. The thermal blanket may be sized to cover selected areas of a patient such as the upper body, including the chest, arms, or shoulders, or the lower body, including the pelvic and groin area and the legs. The warmed air is exhausted underside of the thermal blanket through the apertures provided. The flow of warm air through the apertures occurs at high velocity, thus bringing microbes and dust to the patient by turbulent movement of ambient air flow.

U.S. Pat. No. 7,114,204 to Patrick discloses a method and apparatus for transferring patients. This patient transfer apparatus includes an inflatable mattress, alternatively with a rigid top board with a patient restraint system on which a patient can be placed, when patient immobilization is required. A portable cart is included with a chamber for storage of a plurality of mattresses. The cart also has a gas/air blower and power supply system for empowering the blower. The power system includes provision for drawing power from line AC/DC, and has a rechargeable battery and charger for maintaining the battery by connecting the supply to the line AC/DC. The mattress has a perforated bottom surface for exit of air to provide an air cushion, and is constructed with a white top surface and a dark bottom surface for optimum recognition of contamination, and identification of the bottom, which must be placed downward. The cart is coated with an antimicrobial substance to minimize the risk of contaminants. As shown in the first figure, the patient 90 has been placed on an inflatable mattress 22 for providing an air cushion 96, and the supply system 18 has the hose 26 connected to the air mattress 22 and is supplying a gas, a portion of which is forced out exit holes 82, causing the air mattress 22 to float on a cushion of air/gas 96. An attendant can at this stage, move the air mattress 22 with patient over onto the bed 94. The air mattress disclosed by the Patrick patent is supplied with pressurized air or gas to support the patient lying on the bed. A plurality of holes in the mattress provides on the opposite surface to the one over which the patient is lying, an egress for high velocity air/gas jets which, in turn, provide an air cushion, enabling the bed with the patient to be slid from one location to the other. The air of gas jets provides very strong turbulent air currents stirring up dust and microbes that can infect the patient as well as hospital workers in the operating room. This apparatus is not heated by warm air and does not function in warming the patient.

U.S. Pat. No. 7,837,721 to Augustine, et al. discloses a patient comfort apparatus and system. This apparatus and system thermally comforts a patient; and includes a clinical garment such as a hospital gown, robe, bib, and other equivalents provided with pneumatic, convective thermal treatment for persons or animals. The pneumatic convective device provides convective warming focused or directed primarily on the thorax or body core. The pneumatic convective device includes at least one inlet accessed through a clinical garment, a region in distribution with the inlet for distributing a stream of pressurized, thermally treated air, and a permeable member for emitting pressurized, thermally treated air from the distribution region. As shown in FIG. 1A, the sheets 114 and 116 form between themselves a pneumatic structure to receive and distribute pressurized air within itself. At least one permeable member of the device (the sheet 114, for example) cooperates with the pneumatic structure to emit pressurized air from the device. In this regard, one end of an air hose may be received through an inlet port 127. A stream of pressurized, thermally conditioned air introduced through the air hose fills the space between the sheets 114 and 116 and is distributed throughout the space. The pressurized air is emitted from the pneumatic structure through the air permeable sheet 114. Motion of the emitted air supports heat transfer with a body adjacent, next to or near the pneumatic structure facing the permeable sheet 114. The permeable sheet has holes that deliver the pressurized warm air at high velocity, producing turbulent airflow adjacent to the patient, bringing dust and microbes to the patient.

U.S. Pat. No. 8,414,671 to Augustine, et al discloses personal air filtration devices for use with bedding structures. These devices, methods and systems create a zone of filtered air proximate a patient's head. They include an air filtration device having a blower configured to be disposed within, below, or affixed to a bedding structure; an air plenum in flow communication with the blower and in support of the head of the user and having an air delivery surface configured to distribute the air flow to the zone of filtered air; and a filter disposed within the device for filtering the air flow before it is distributed to the zone of filtered air. Filtered air is exhausted, surrounding the patient and producing airflow that is turbulent and can deliver microbes and dust to the patient. There is no sterilization of the interior of the blower, as recommended by the FDA.

It has been found that sterilization of forced-air blowers utilized for warming blankets and mattresses is necessary and has been specifically recommended by the FDA. Standards being implemented require frequent cleaning and sterility owing to findings that contaminated forced-air can increase the concentration of contaminated airborne particles over a surgical site. Despite the finding that forced-air blowers need regular maintenance and cleaning, the current cleaning method typically involves simply wiping down the blower device. Wipe-down of the blower frequently fails to clean the inside of the blower itself, and therefore forced-air from the blower typically poses contamination threats to the surgical site when the forced-air blower is being used with patient warmers or lifters.

Based on the foregoing, there exists a need in the art for improved sterility of the internal components of non-closed circuit forced hot air warmers/blowers, thereby mitigating and/or preventing infections of patients when the blower is being utilized, as well as decreasing exposure of contaminants of operating room hospital workers.

SUMMARY OF THE INVENTION

The present invention provides a system for an antimicrobial mist generator for use as a stand-alone internal sterilizer for closed circuit and open circuit forced hot air warmers/blowers that deliver heated air to patient's beds and blankets with improved sterility. An antimicrobial mist generator is in-line with a forced-air warmer to circulate sterilized heated air within the internal components of the warmer/blower forming a closed system during the process. It may be employed in a closed system device or in a non-closed system device that is temporarily adapted to connect to the mist generator for disinfection. The mist generator delivers misted warmed air saturated with a sanitizer into the internal components of the blower to clean and sterilize the components. During later use of the blower, this sanitation of the internal components prevents unsterile air currents containing microbes from being delivered from the blower when it is in-line with a patient warmer or lifter, thereby decreasing the risk of infection from blower contaminants.

Briefly stated, the mist generator is operable with a closed or non-closed circuit forced hot air warmer to provide misted sterilized hot air for cleaning a blower that, in turn is employed for warming a patient bed or blanket, preventing hypothermia of the patient that may significantly increase healing time periods, and/or to provide internal sterilization of the patient bed or blanket. Warm air is supplied from a blower which has been internally sterilized. The inlet and outlet ports of the blower are guarded with a HEPA filter having a pore dimension less than 0.22 microns to prevent the entry of microorganisms or dust particles. The temperature of warm air, its pressure and flow rate are controlled by a control panel set by the operator of the device.

In a first embodiment, the mist generator for improved sterility of blowers having controlled forced air comprises a main body having a top wall with an opening, the opening traversing into a chamber adapted to receive a disinfectant, side walls and a bottom wall. The main body further includes an inlet duct adapted for attachment to a first hose which in turn is adapted for attachment to an output opening of the blower for delivery of forced air into the chamber to carry disinfectant misted air. The main body also includes an output duct adapted for attachment to a second hose which in turn is adapted for attachment to a blower inlet opening of the blower for delivery of disinfectant misted air through internal components of the blower. whereby the mist generator improves sterility of the blower to mitigate microbial contamination of patient warmers and lifters and hospital environments. The blower can be in a closed or a temporarily closed, non-closed system with microprocessor controlled air heating capability.

An improvement in sterilizing of temporarily closed, non-closed circuit patient warmers is provided, the improvement comprising: a mist generator containing a disinfectant constructed having an inlet duct traversing to a chamber having a chamber containing the disinfectant; an output duct adapted for attachment to a second hose which in turn is adapted for attachment to a blower inlet opening of the blower for delivery of disinfectant misted air through internal components of the blower; the inlet duct being adapted to be connected to a blower with controlled air delivery capability to form a temporary closed circuit and run a sterilization cycle for a preselected time period.

BRIEF DESCRIPTION OF THE DRAWING

The invention will be more fully understood and further advantages will become apparent when reference is had to the following detailed description of the preferred embodiments of the invention and the accompanying drawing, in which:

FIG. 8 illustrates the embodiment of FIG. 7 connected to a blower with air warmer machinery and flexible tubes being sterilized by the antimicrobial/disinfectant mist generator;

FIG. 9b illustrates another embodiment of a spray capsule/cartridge adapted to be inserted within the mist generator of FIG. 9a;

FIG. 9c illustrates an embodiment of a capsule/cartridge adapted to be inserted within the mist generator of FIG. 9a;

FIG. 9d illustrates another embodiment of a capsule/cartridge adapted to be inserted within the mist generator of FIG. 9a;

DETAILED DESCRIPTION OF THE INVENTION

Figure 1:
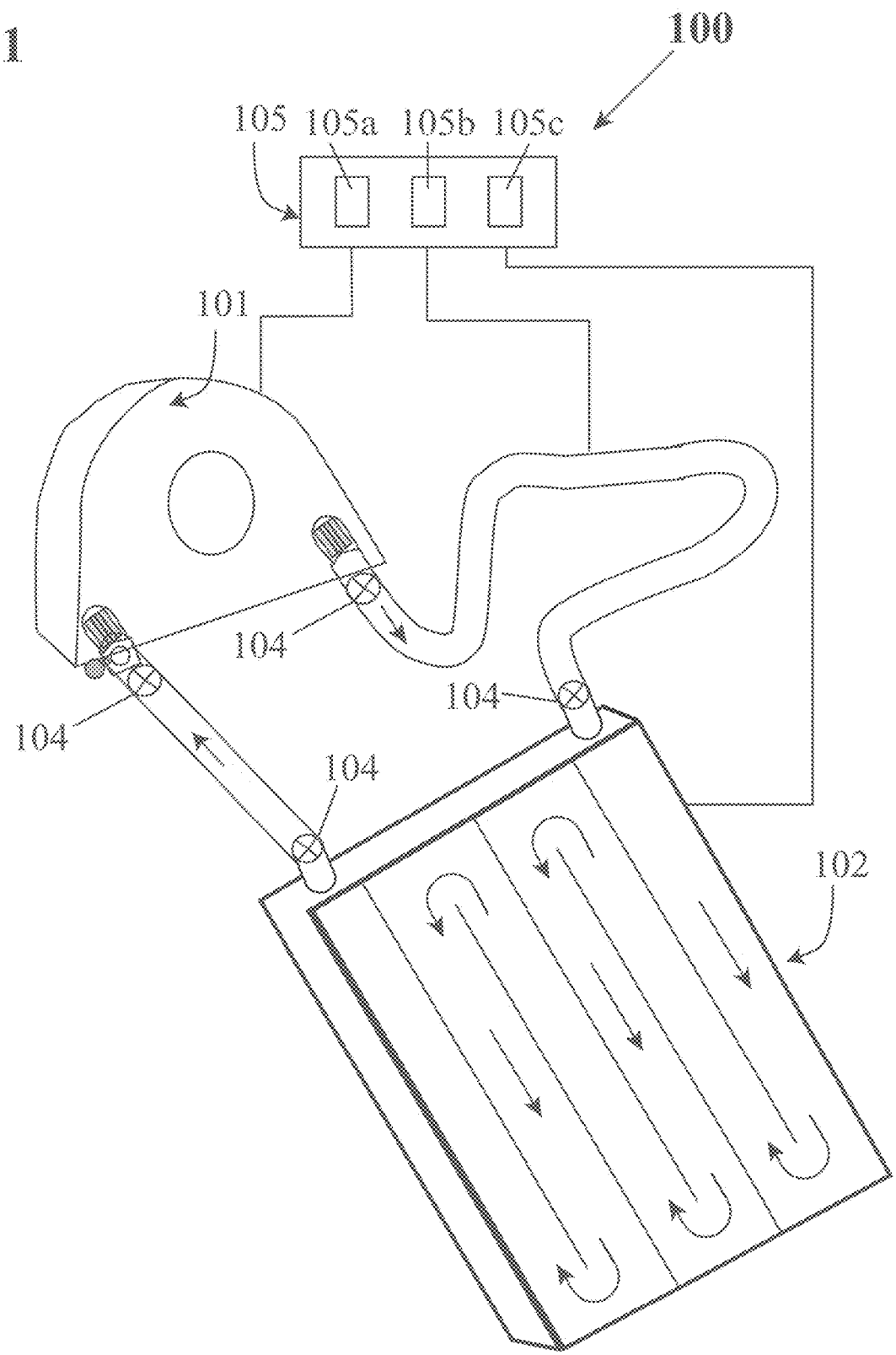
FIG. 1 illustrates an embodiment of a system for delivering warm air to patient beds and blankets in a closed circulating circuit.

The objective of the invention is to provide a mist generator for delivering an antimicrobial or disinfectant mist to a blower in order to sterilize the blower for later use with patent warmers and/or patient lifters, thereby decreasing the possibility of patients suffering infections and hospital workers in the operating room being exposed to infecting microbes. The subject mist generator is intended to perform internal sterilization of the blower and hoses of a patient warmer or lifter. As the mat is single use and disposable, it is not necessary for the mist generator to disinfect it, though the generator may be employed when the mat is connected. The generator must be used in a closed circuit, although that may be only temporary. Disinfectant or antimicrobial is introduced into the chamber and vaporized by warm air circulated by the blower. After the disinfectant sterilizes the inside surfaces of the blower and hoses, an aliquot of water is introduced into the chamber and is similarly vaporized, taking up the disinfectant residue. A dry desiccant is then appointed to be introduced into the chamber and absorbs the mist. After the mist is absorbed and the system is clean and dry, the blower is then turned off. The mist generator is removed from the system and discarded, if it is disposable; or, if not disposable, is simply emptied.

The subject antimicrobial or disinfectant mist generator is operable as a stand-alone internal sterilizer for non-closed-circuit patient warmers. Internal sterilization of the patient warmers through use of the antimicrobial mist generator mitigates infection risks caused from contaminated air flow of the patient warmer. An outflow/output duct of the antimicrobial mist generator is attached to a flexible hose that connects to an air inflow duct of any non-closed circuit device, temporarily making it run as a closed circuit and allowing internal sterilization, including drying, without releasing disinfectant vapor into the hospital environment. The antimicrobial mist generator, is preferably, but not necessarily, disposable; and achieves the internal sterilization that is currently impossible with patient heating devices now in use. The FDA has recommended "regular cleaning" of patient heating devices, therefore the subject antimicrobial mist generator provides an add-on stand-alone internal sterilizer for ready compliance with FDA recommendations. In one embodiment, the antimicrobial mist generator avoids a port into its chamber that could be opened for filling, and instead is constructed to have a soft diaphragm through which fluids are introduced with a needle and syringe, similar to medicine vials, in order to avoid contamination. Desiccant is then introduced into the chamber via a removable port.

The term non-closed circuit or open circuit refers generally to blowers having an outlet air duct for delivering forced air to a perforated blanket and an air inlet duct for pulling air from the atmosphere into the blower and no return of warm air to the blower. As used herein, the term closed circuit refers generally to a pathway wherein there is a closed loop with no waste outlet or perforation of the blanket with all air returned via a separate duct to the blower.

Measurements have shown that a surgical patient under an aesthesia loses about 1.6 degrees C. body temperature during the first hour. Such body temperature loss can lead to hypothermia, shivering and may compromise the patient's healing ability. [See http://solutions.3m.com/wps/portal/3M/en_EU/Healthcare-Europe/EU-Home/Products/InfectionPrevention/Patient_Warming/.] Patient warming beds and warming blankets are essential to prevent this onset of patient hypothermia.

For the past two decades, maintenance of patient body temperature during surgery has largely been achieved with forced hot air warming; this process replaced circulating hot water blankets, which were cumbersome and often ruptured, covering the floor with water. Tent, blanket and mattress designs have also been used. Virtually all of these have been inexpensive and disposable, and have attempted to avoid the problem of difficult and often incomplete cleaning between uses. All of the currently used forced hot air devices have a blanket or pad with multiple holes that emit the warmed air around the patient or an open tent over the patient into which the warm air is blown. Some recent studies have documented that the release or leakage of the forced air causes unwanted air currents that bring up potentially unclean air from near the floor or cause increased numbers of particles and bacteria to circulate over the prepped area of the surgical incision, increasing the risk of operative infection. Examination has also revealed bacteria collecting within the blowers. Another study demonstrated that the air currents interfere with the laminar airflow sometimes used in the operating room to discourage bacterial contamination. The FDA has also recently released an alert, describing their concerns and the need for a regular program of cleaning and maintenance of heater/cooler devices. While the contention that these devices are related to an increase in operative infections has been questioned, it seems reasonable to attempt to avoid air leakage and any possibly undesirable air currents that might increase infection risk. Avoiding the buildup of bacteria within the blower is obviously a reasonable goal. Bacterial contamination related to increased infection has recently been reported in the liquid of water blankets. Staying with a forced hot air system that employs inexpensive, disposable mattresses and blankets that do not need to be cleaned is clearly desirable.

Recently FDC has issued the following warning located at http://www.medscape.com/viewarticle/852750 which is reproduced below:

FDA Warns Infections a Risk With Heater-Cooler Devices
Megan Brooks
Disclosures|Oct. 15, 2015

The use of heater-cooler devices has been associated with nontuberculous mycobacterium (NTM) infections, primarily in patients undergoing cardiothoracic surgeries, the US Food and Drug Administration (FDA) warned today.

Heater-cooler devices are used during medical and surgical procedures to warm or cool a patient, as appropriate. The devices include water tanks that provide temperature-controlled water to external heat exchangers or warming/cooling blankets through closed circuits.

Although the water in the circuits does not come into direct contact with the patient, there is the potential for contaminated water to enter other parts of the device or transmit bacteria through the air, via the device's exhaust vent, into the environment and to the patient, the FDA notes in a safety communication posted on its website. Between January 2010 and August 2015, the FDA received 32 reports of patient infections associated with heater-cooler devices or bacterial heater-cooler device contamination, with 25 reported this year.

"Some reports describe NTM infections related to cardiothoracic surgeries, but other reports do not specify the procedure the patient was undergoing," the FDA notes. Eight reports were related to three events describing patient infections occurring in US healthcare facilities, whereas the other 24 reports involved facilities outside the United States, mostly in Western Europe.

In some cases, patients presented with infections several months to years after their surgical procedure. The FDA is not aware of NTM infections acquired by hospital staff.

The FDA says it is "actively" monitoring the situation and will provide updates as appropriate.

The aim of today's safety communication is to "heighten awareness about infections associated with heater-cooler devices and steps health care providers and health facilities can take to mitigate risks to patients," they say.

Recommendations

In addition to following standard precautions, the FDA recommend that healthcare facilities and staff using heater-cooler devices consider implementing the following measures to reduce risk to patients:

Strictly adhere to the cleaning and disinfection instructions provided in the manufacturer's device labeling. Ensure you have the most current version of the manufacturers' instructions for use readily available to promote adherence.

Do not use tap water to rinse, fill, refill or top-off water tanks, as this may introduce NTM organisms. Use only sterile water or water that has been passed through a filter of less than or equal to 0.22 microns. When making ice needed for patient cooling during surgical procedures, use only sterile water or water that has been passed through a filter of less than or equal to 0.22 microns. Deionized water and sterile water created through reverse osmosis is not recommended because it may promote corrosion of the metal components of the system.

Direct the heater-cooler's vent exhaust away from the surgical field to mitigate the risk of aerosolizing heater-cooler tank water into the sterile field and exposing the patient.

Establish regular cleaning, disinfection, and maintenance schedules for heater-cooler devices according to the manufacturers' instructions to minimize the risk for bacterial growth and subsequent patient infection.

Develop and follow a comprehensive quality control program for maintenance, cleaning, and disinfection of heater-cooler devices. Your program may include written procedures for monitoring adherence to the program and documenting set up, cleaning, and disinfection processes before and after use.

Immediately remove from service heater-cooler devices that show discoloration or cloudiness in the fluid lines/circuits, which may indicate bacterial growth. Consult your hospital infection control officials to perform the appropriate follow-up measures and report events of device contamination to the manufacturer.

Consider performing environmental, air, and water sampling and monitoring if heater-cooler contamination is suspected. Environmental monitoring requires specialized expertise and equipment to collect and process samples, which may not be feasible in all facilities.

Healthcare facilities should follow their internal procedures for notifying and culturing patients if they suspect infection associated with heater-cooler devices.

The present invention addresses the aforementioned issues by providing an antimicrobial mist generator operable as a stand-alone internal sterilizer for closed and non-closed-circuit blowers. Internal sterilization of the blower through use of the antimicrobial mist generator mitigates infection risks caused from contaminated air flow of the patient blower when it is being used with patient lifters and/or warmer devices. An outflow chamber/output duct of the antimicrobial mist generator is attached to a flexible hose that connects to an air inflow of any non-closed circuit device, temporarily making it run as a closed circuit and allowing internal sterilization, including drying, without releasing disinfectant vapor into the hospital environment. The antimicrobial mist generator, presumably, but not necessarily disposable, achieves the internal sterilization that is currently impossible with the patient heating devices now in use.

When the antimicrobial mist generator is in-line with a patient warming device circulating heated controlled warm air, the warm air passes through the antimicrobial mist generator and become substantially saturated by evaporated disinfectant forming an aerated mist. As warm air carrying sterilizing mist passes through the non-closed circuit patient warmer device the disinfectant kills harmful bacteria and germs so that the non-closed circuit patient warmer device's internal chambers are substantially free of bacteria and germs, thereby decreasing infection risks. Non-closed circuit patient warmer devices include, for non-limiting example, sterilized blowers with microprocessor controlled air heating capabilities.

The disinfectant utilized has a high volatility so that it is capable of evaporating and forming a saturated misted air flow up on application of the warm air pressure, yet substantially evaporating and dissipating to internally sterilize the non-closed circuit patient warmer device. The warming system circulates all of the warmed air within a non-closed circuit to provide internal sterilization, so that sterilized warmed air is released outside the non-closed warm air circulating system. Preferably, the disinfectant is a volatile liquid component that is adapted to vaporize as forced air blows over said disinfectant. Volatile liquid components preferably include alcohol-based solutions, containing one or more of isopropyl alcohol, ethanol (ethyl alcohol), and n-propanol solutions containing 60% to 95% alcohol. Non-alcohol based solutions may contain benzalkonium chloride or triclosan. Alternatively, the disinfectant may be a volatile liquid component saturated within a porous substrate, such as a sponge, capsule, cartridge or filter, and said liquid vaporizes and escapes the substrate as forced air blows over said substrate. The disinfectant may be in an aqueous solution with alcohol solution or antiseptic therein.

The mist generator may include a transducer facilitating formation of the disinfectant mist, such as a piezoelectric transducer device including a transmitter, receiver or sensor, for converting high frequency electronic signals into high frequency mechanical vibration. The disinfectant (typically aqueous solution) cavitates into vapor which is forced through the surface of the disinfectant as a very fine mist, which is easily absorbed into the air flow. See for example http://www.piezo-ultrasonic.com/piezoelectric-transducer-applications-a006.html.

The closed circuit of the warming system is sterilized with antimicrobial disinfectant spray or atomized mist. The warm air contained in the closed circulating system is sterile. At the end of use of the bed or blanket, the system can be sterilized with antimicrobial disinfectant atomized mist if desired and the disposable bed or blanket discarded.

The closed circuit forced hot air warmer consists of a blower connected by flexible conduit using quick connect couplings to a terminal device, which may be a blanket or a mattress that is not an open tent. The air that enters the terminal device passes through a HEPA filter with a pore size less than 0.22 microns to catch any bacteria or particles in the incoming airflow. The warm air passes through a structured chamber, or a folded tube within the chamber, so that the blanket or mattress is filled with warm air that passes slowly through the device to an outflow port and returns back to the blower in a completely closed system. There are no apertures to release warm air and no air leaks from the system, avoiding possible turbulence and air currents in the operating room. The internal chamber structure insures that warm air is not shunted to the outflow port, but rather fills the entire chamber, so that the entire device remains warm, transmitting heat to the patient by direct contact and maintaining body temperature. The return air conduit is detachable from the device, as well. The blanket or mattress, therefore, remains a simple, inexpensive device and is suitable for disposal after use.

The HEPA filters at the inflow and outflow portals of the blower and the fact that each disposable pad is clean help to avoid bacterial contamination. The unique design of the system makes sterilization of the air channels in the blower and the connecting tubes easy to perform. The detached ends of the flexible inflow and outflow lines are each connected to a small (detachable) chamber. A measured amount of liquid disinfectant is introduced through a separate port and the blower is turned on. The circulating air will take up the disinfectant, which will be carried through the system as an aerosol. After a brief period, all internal surfaces are disinfected. A second aliquot of STERILE distilled water can be added later to rinse out the system. Following the two steps, a desiccant, paper or sponge is introduced and the blower again turned on. Any residual liquid is caught in the dry material. The two conduits are then disconnected, the chamber discarded or emptied and the sterilized system is ready for use.

A filtered port allows ambient air to enter the blower at the beginning of a cycle. When the system has been filled and air begins to return via the outflow conduit, the entry portal closes automatically or is capped and only air from the outflow conduit can enter the blower for recirculation.

FIG. 1 illustrates at 100 a system for delivering warm air to patient beds and blankets in a closed circulating circuit. The closed circuit warm air delivery system comprises a blower 101 with microprocessor controlled temperature, pressure and flow control that has input and output ports each guarded by HEPA filters. The blower output port is connected to the input port of patient bed or blanket 102 using by flexible tubing with quick release connectors 104. The output port of the patient bed or blanket is connected to the input port of the blower 101 using flexible tubing again with quick release connectors 104. The microprocessor control panel is shown at 105. The microprocessor controls the warm air temperature at 105*a* warm airflow rate at 105*b* and warm air pressure at 105*c*. The warm airflow path is therefore a continuous closed circuit with no warm air escape location. The airflow rate is proportional to the speed of rotation of the blower motor. The electrical current supplied to the heating elements controls the warm air temperature.

Figure 2:
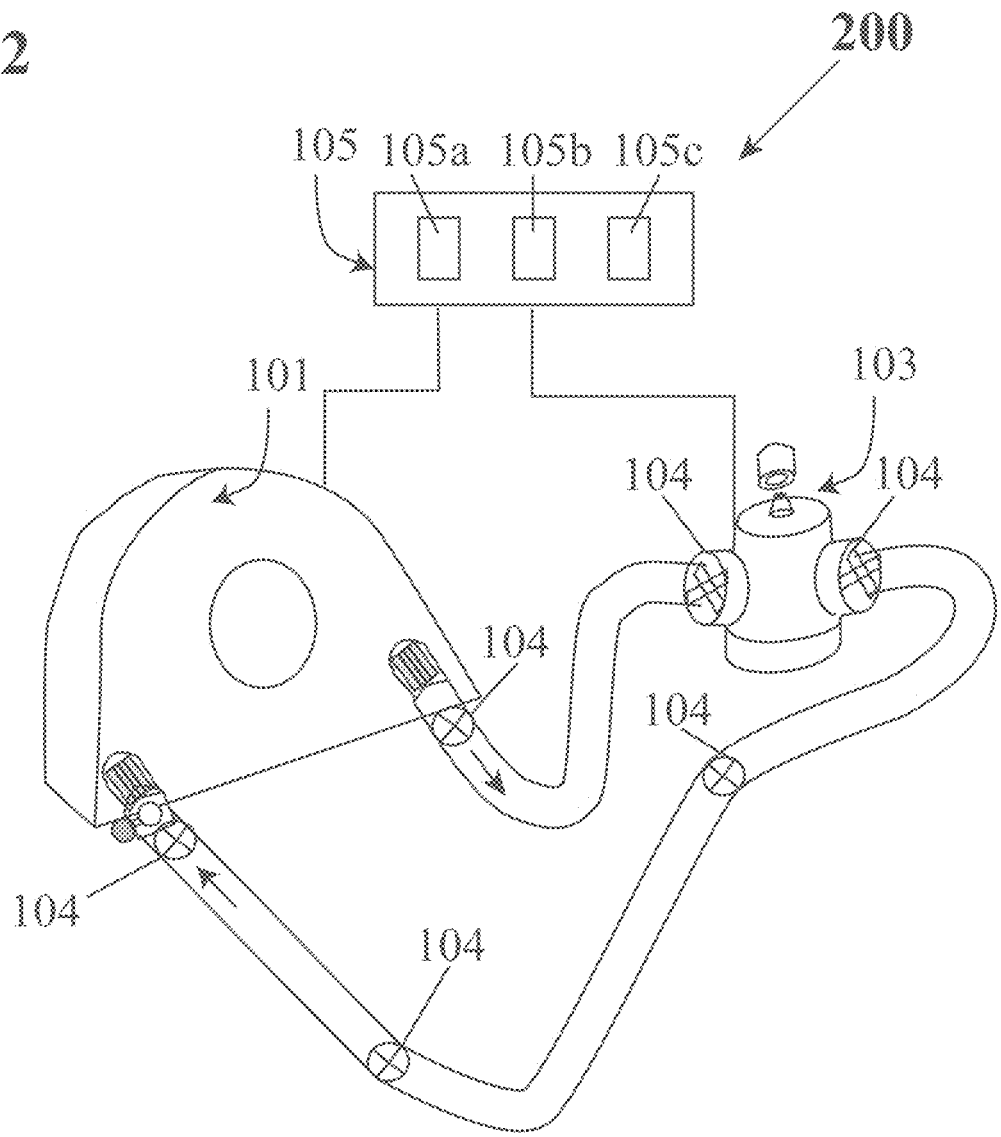
FIG. 2 illustrates an embodiment of the blower with air warmer machinery and flexible tubes being sterilized by the antimicrobial mist generator.

FIG. 2 illustrates at 200 the blower with air warmer machinery and flexible tubes used being sterilized by the antimicrobial mist generator. The blower with air warmer machinery is shown at 101 with HEPA filters both at inlet and outlet. The output of the blower is connected to the inlet of the antimicrobial mist generator 103 using a flexible hose provided with quick release couplings. The output of the antimicrobial mist generator 103 is connected to the inlet port of the blower 101 using a flexible hose provided with quick release couplings. The antimicrobial solution in the antimicrobial mist generator is atomized and circulated in this closed path for a preselected time period, which may be as long as 15 minutes, disinfecting circuit sterilizing the blower with air warming machinery 101 and all the flexible hoses in the system. At the end of this disinfecting step, the quick release couplings are disconnected and reattached to the blower and the mat. Any moisture present in the blower 101 and flexible hoses can be blown into a dry sponge.

Figure 3:
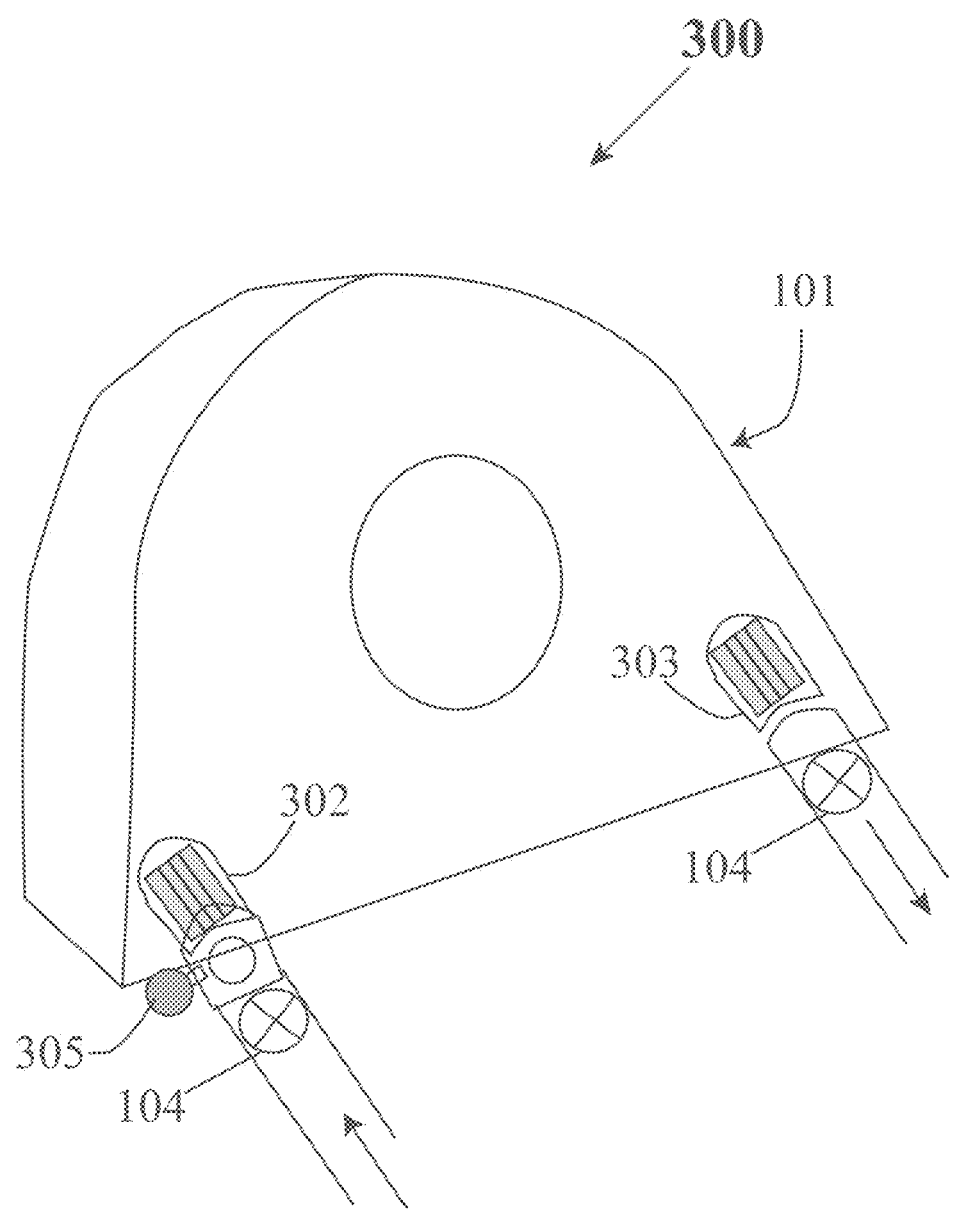
FIG. 3 illustrates details of an embodiment of the microprocessor controlled blower with input port 202 and an output port, both provided with HEPA filters.

FIG. 3 illustrates at 300 the details of the microprocessor controlled blower with warm air delivery 101. As illustrated, the blower has input port 302 and output port 303 both provided with HEPA filters. The quick release connectors of the flexible hose are shown at 104. The warm air flow bath is indicated by the arrows. The blower with warm air delivery has a blower fan and electrical heating elements with sensors for air temperature, air pressure and air low rate communicating with the microprocessor control as shown in FIG. 1.

Figure 4:
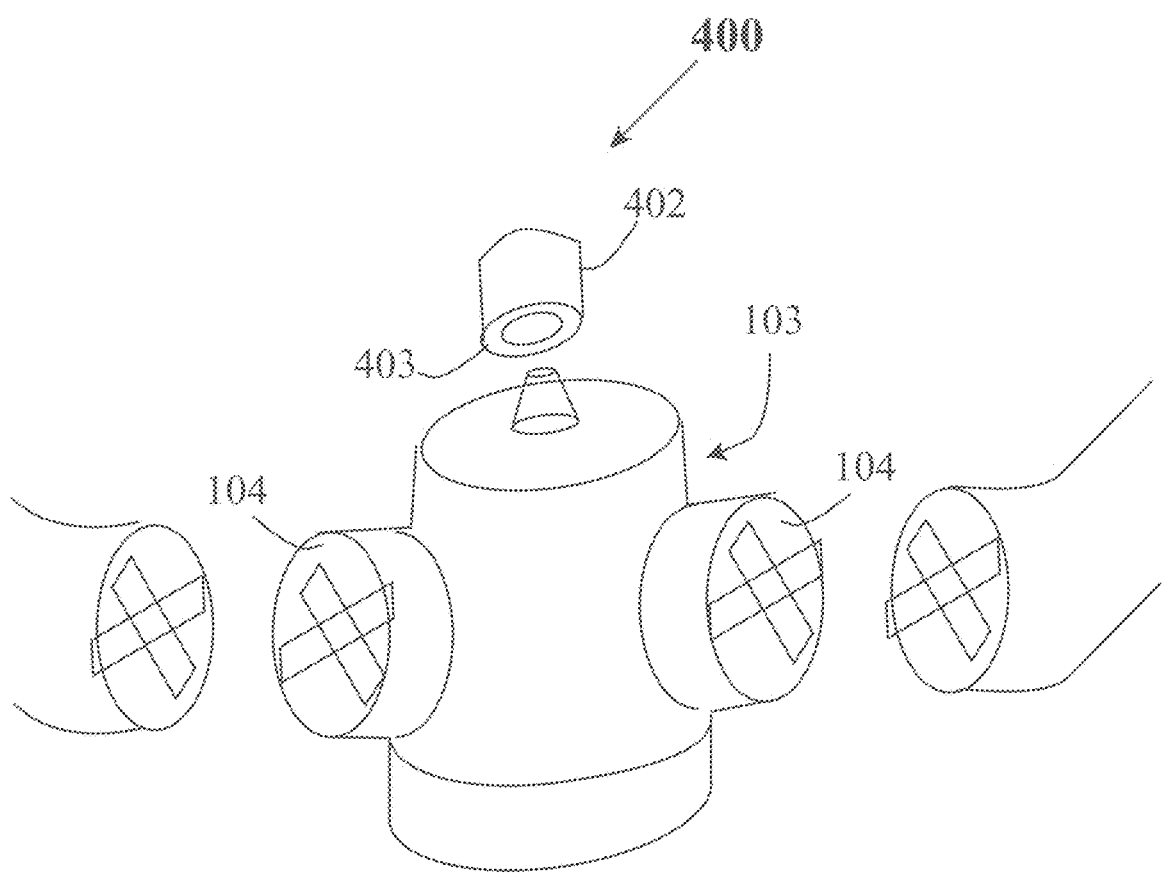
FIG. 4 illustrates an embodiment of the antimicrobial mist generator.

FIG. 4 illustrates at 400 an embodiment of the antimicrobial mist generator, which is only used to achieve internal sterilization of the blower warm air machinery 101 and all the flexible hoses used. The mist generator is filled with a capsule 402 that has the antimicrobial liquid sealed with gasket 403, which is atomized by the flow of warm air through the input port and is delivered to the output port. In an alternative embodiment a microprocessor may be provided which preferably turns on the antimicrobial mist spray during initial set up to sterilize the interior surfaces of blower and flexible tubes. When the sterilization operation is complete, an aliquot of sterile distilled water is introduced and any residual disinfectant is vaporized in the circulated water vapor. Any remaining water can be taken up into a clean sponge or desiccant. Quick release couplings 104 connect the flexible hoses to the inlet and outlet of antimicrobial mist generator 103. The mist generator is then disconnected from both flexible hoses and discarded.

Figure 5:
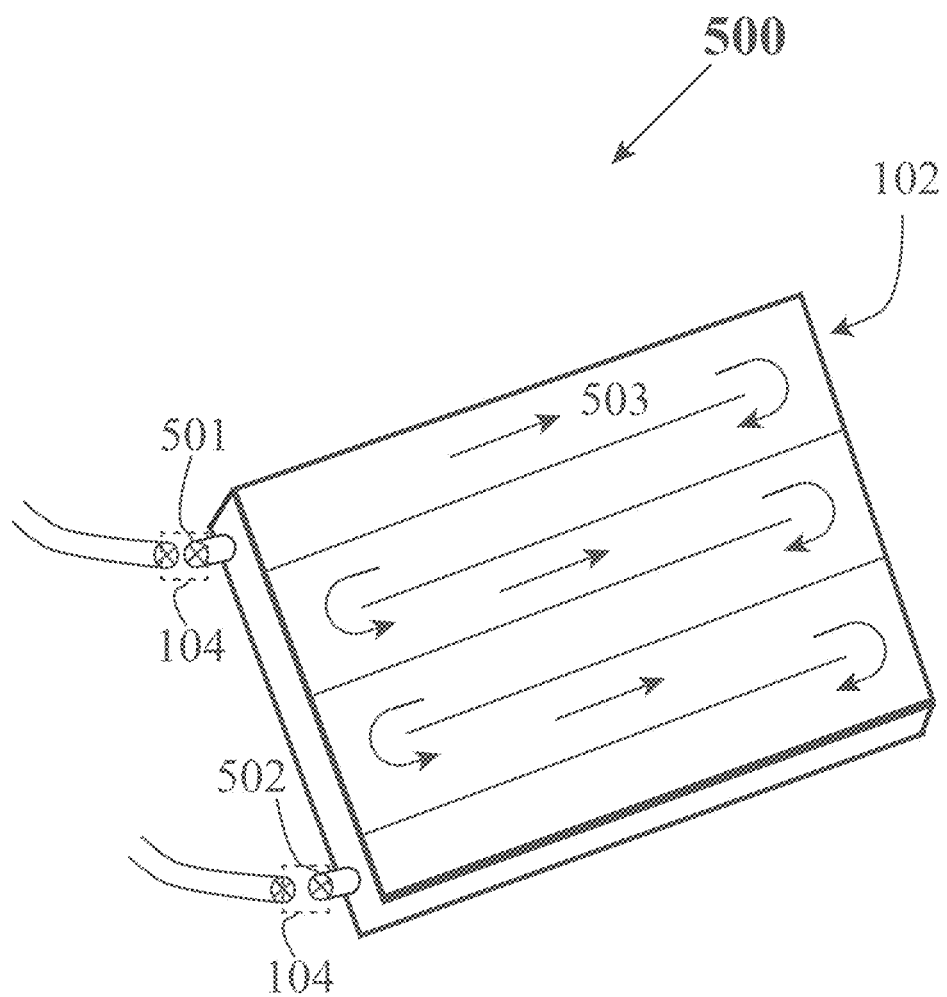
FIG. 5 illustrates an embodiment of the patient mattress or blanket.

FIG. 5 illustrates at 500 the patient bed or blanket 102 for a closed system. The inlet of warm air into the bed or blanket is shown at 501. The patient bed or blanket has a plurality of interconnected airflow paths indicated by arrows shown at 503. The outlet of the patient bed or blanket 102 is shown at 502. The connection of flexible hose to the inlet and outlet is done using quick release couplings 104.

Figure 6:
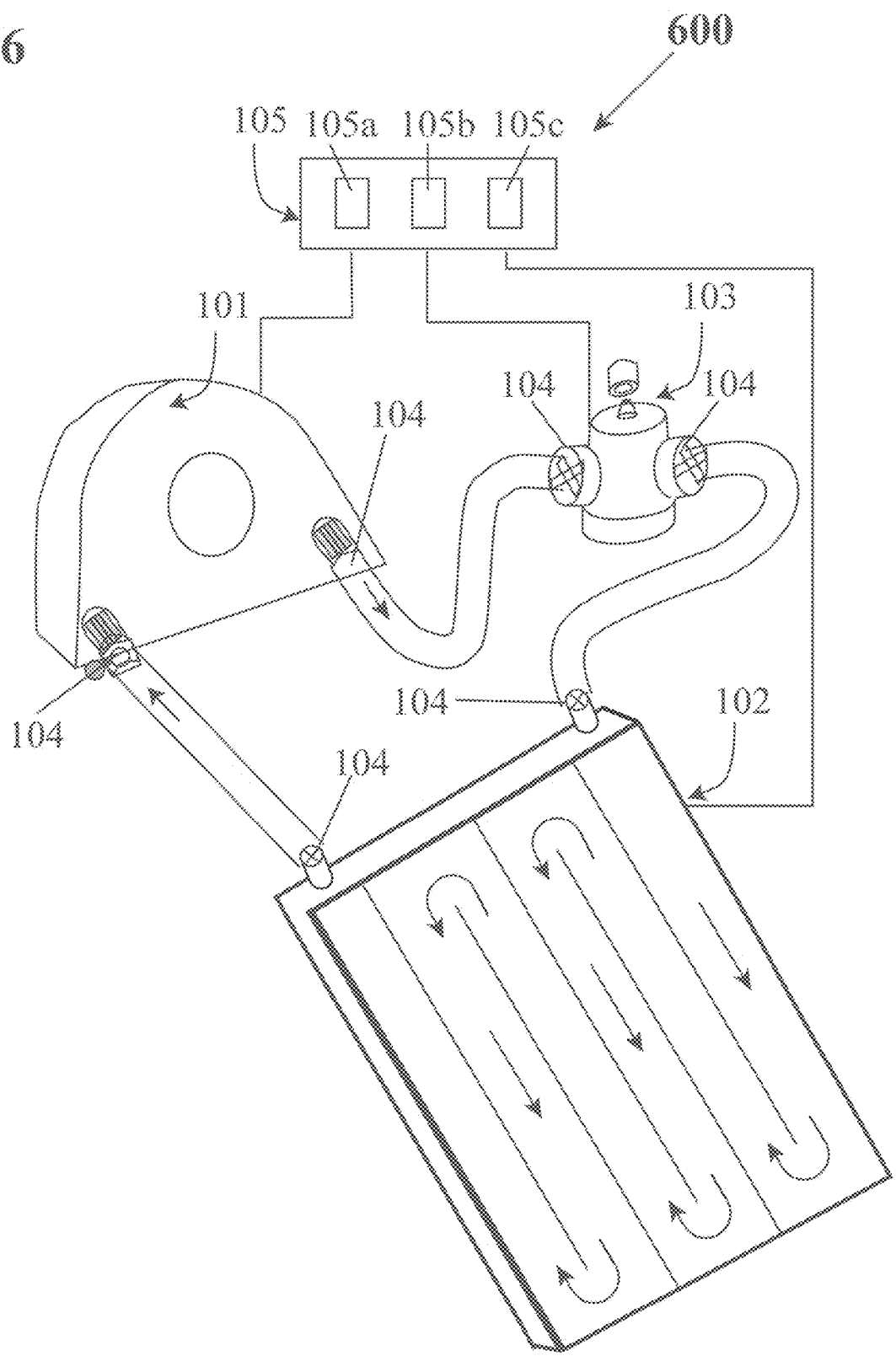
FIG. 6 illustrates an embodiment of the sterilization process of the patient bed or blanket prior to disposal.

FIG. 6 illustrates at 600 an optional arrangement for the sterilization process of patient bed or blanket. This is similar to FIG. 1 except that the antimicrobial mist generator 103 is inserted between the blower warm air machinery 101 and the patient bed or blanket 102 and a closed circuit is formed using flexible hoses with quick release connectors 104. When used prior to disposal, the sterilization process can be run for about 15 minutes and the sterilized patient bed or blanket is then discarded.

Figure 7:
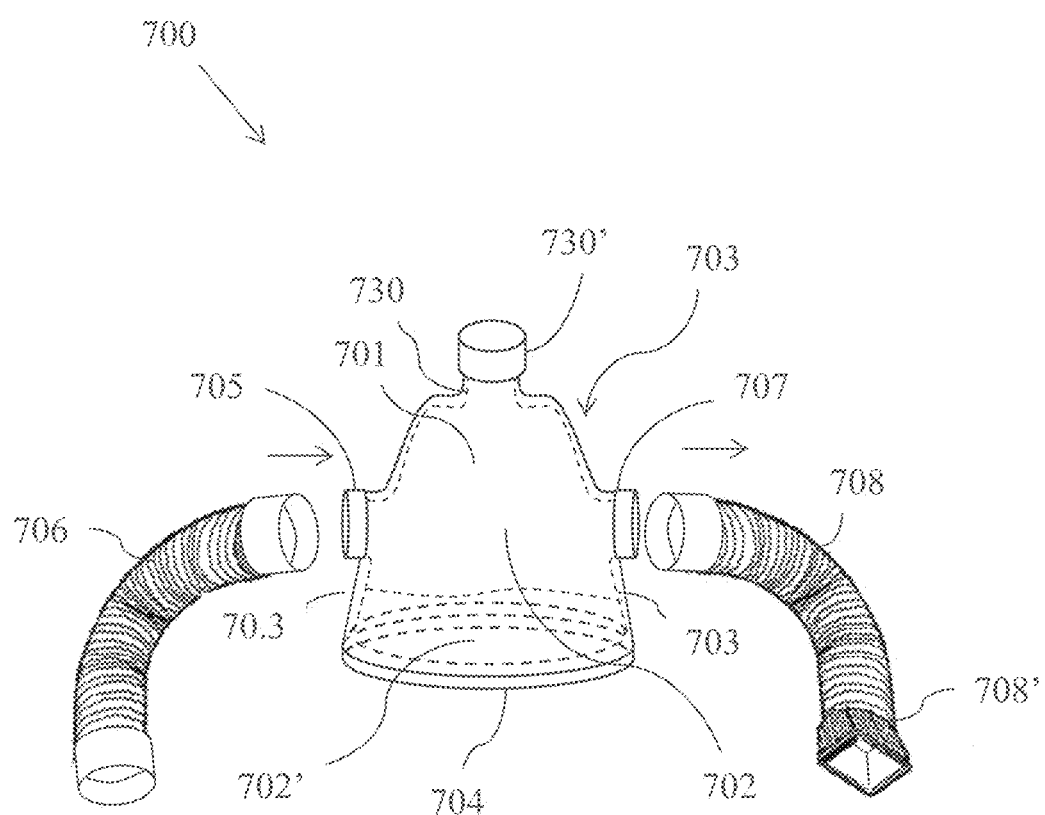
FIG. 7 illustrates another embodiment of the microprocessor controlled antimicrobial mist generator.

FIG. 7 illustrates another embodiment of the microprocessor controlled antimicrobial mist generator, shown generally at 700. FIG. 8 illustrates the embodiment of FIG. 7 in-line with a non-closed circuit blower, shown generally at 800, forming a temporarily closed circuit.

Referring to FIGS. 7 and 8, the antimicrobial mist generator 703 is only used to achieve internal sterilization of the blower warm air machinery and all the flexible hoses associated therewith. The mist generator comprises a main body 701 having a top wall 730 with an opening 730' with a removable cap, the opening traversing into a chamber 702 adapted to receive a disinfectant shown generally at 702' (misting shown in FIG. 8 at 702"), side walls 703 and a bottom wall 704 that may include a bottom cover to allow access into the chamber of the main body for inserting and later removing desiccant and the like. The main body 701 further includes an inlet duct 705 adapted for attachment to a first hose 706 which in turn is adapted for attachment to an output opening 711 of a blower 710 for delivery of forced air into the chamber 702 to carry disinfectant misted air. The main body 701 also includes an output duct 707 adapted for attachment to a second hose 708 which in turn is adapted for attachment to a blower inlet 712 opening of the blower 710 for delivery of disinfectant misted air through internal components of the blower 710 to improve sterility of the blower 710 to mitigate microbial contamination of patient warmers and lifters and hospital environments when the blower is in use. Second hose 708 is attached to the blower inlet 712 by way of an attachment or modification to the inflow of the blower to accept that hose, shown generally at 708'. The blower with air warmer machinery is shown at 710 with HEPA filters at each inlet 712 and outlet 711.

The top wall opening 730' is preferably includes a narrow (~5 cm) neck closed with a removable cap so that disinfectant, water, dry desiccant, etc., can be introduced through the neck/opening 730'. Owing to the narrow neck and opening 730', desiccant and other bulky solids cannot be easily removed, and therefore re-use is avoided. However, if the mist generator is not disposable, the bottom wall may include a bottom cap/base that is removable by screwing same off to permit emptying of the mist generator.

Capsule or chamber 702 has the antimicrobial or disinfectant liquid sealed with a gasket/diaphragm preferably at opening 730'. The liquid is atomized by the flow of warm air through the input port and is delivered to the output port. In an alternative embodiment, a transducer for misting the liquid may be provided. The antimicrobial mist generator may be microprocessor controlled wherein the controls turn on an antimicrobial mist spray during initial set up to sterilize the interior surfaces of blower air machinery and flexible tubes attached thereto. When the sterilization operation is complete, an aliquot of sterile distilled water is introduced and any residual disinfectant is vaporized in the circulated water vapor. Any remaining water can be taken up into a clean sponge or desiccant. Quick release couplings 104 connect the flexible hoses to the inlet and outlet of antimicrobial mist generator 103. The mist generator is then disconnected from both flexible hoses and discarded.

The antimicrobial mist generator is capable of being utilized as a stand-alone internal sterilizer for non-closed-circuit patient warmers. Antimicrobial mist generator includes a mist chamber for housing a disinfectant adapted to vaporize or form a mist upon contact with warm air. Preferably the outflow/outlet of the chamber is attached to flexible hose 704 connected to any non-closed circuit device, temporarily making it run as a closed circuit and allowing internal sterilization, including drying, without releasing disinfectant vapor into the hospital environment. The generator, presumably, but not necessarily disposable, would achieve the internal sterilization that is currently impossible with the blower devices now in use.

Flexible hoses (fixed or detached) are attached to the mist generator via the inflow part of a warmer that is not closed circuit, creating a temporary closed circuit that allows internal sterilization. An aliquot of sterile water can be introduced after the sterilization takes place to remove residual disinfectant. A sponge or descant is inserted and the system again run to remove residual liquid/vapor.

FDA required "regular cleaning" of patient heating devices can be achieved with the subject system without changing any other components. Heated air takes up the fluid within the chamber whereupon it continues traveling with the warm forced air as a mist or vapor through tubes to sterilize devices attached thereto. Fluids contemplated include chemicals compositions having relatively low boiling points or volatility so that the disinfectant vaporizes upon being heated by way of the warm air. Examples include alcohols such as ethanol etc.

Figure 9A:
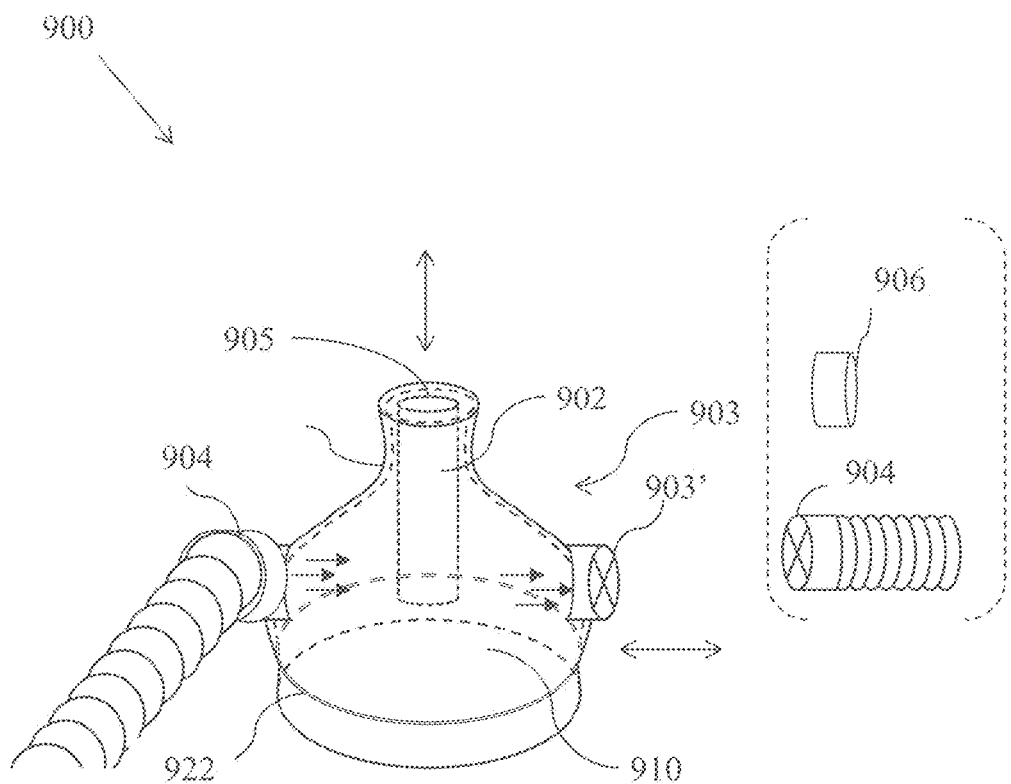
FIG. 9a illustrates another embodiment of the antimicrobial mist generator.

FIG. 9a illustrates another embodiment of the antimicrobial mist generator, shown generally at 900. The antimicrobial mist generator 903 is generally used to achieve internal sterilization of the blower warm air machinery and all the flexible hoses used. The mist generator is filled with a capsule 902 that has the antimicrobial liquid sealed with gasket/diaphragm 905, which is atomized by the flow of warm air through the input port and is delivered to the output port. The antimicrobial mist generator 903 turns on the antimicrobial mist spray during initial set up to sterilize the interior surfaces of blower air machinery and flexible tubes attached thereto. When the sterilization operation is complete, an aliquot of sterile distilled water may be introduced and any residual disinfectant is removed in the circulated water vapor. Quick release couplings 904 connect the flexible hose to the inlet of antimicrobial mist generator 903. Antimicrobial mist generator 903 preferably includes an outlet 903' whereupon either a cap 906 or a quick release coupling 904 connecting to a flexible hose is preferably provided for connection of the mist generator 903 to patient warmer devices including for example blower warm air machinery (see FIGS. 2 and 10), or a mattress or a bed for sterilization thereof (see FIG. 6). The mist generator is disconnected from both flexible hoses after the system is dried internally by running the blower, and excess water is taken up into a clean sponge or desiccant.

The antimicrobial mist generator 903 is capable of being utilized as a stand-alone internal sterilizer for non-closed-circuit patient warmers (such as without limitation the kind use by 3M associated with the trade name BAIR and others). Antimicrobial mist generator 903 includes a mist chamber 910 for housing a disinfectant adapted to vaporize or form a mist upon contact with warm air. In this use, the outflow/outlet 903' of the chamber 910 is attached to flexible hose 904 connected to a non-closed circuit device, temporarily making it run as a closed circuit and allowing internal sterilization, including drying, without releasing disinfectant vapor into the hospital environment (See FIG. 10). The generator, presumably, but not necessarily disposable, would achieve the internal sterilization that is currently impossible with the patient heating devices now in use. Preferably the mist generator 903 is shaped having a neck portion 921 at the top with a diameter substantially less than the diameter of a bottom portion 922. Preferably, neck portion 921 has a diameter of approximately 5 cm, which is substantially less than the diameter of a bottom portion 922 which in turn preferably includes curved walls so that the bottom portion is substantially bulbous. The bottom portion 922 may include a bottom opening with a removable bottom cover 923 that affords access to the chamber of the mist generator to allow addition and later removal of desiccant or fibers that can absorb circulating moisture, the cover 923 being necessary only if the mist generator is designed and employed for multiple use. The preferred embodiment is for the bottom portion to be solid, making it difficult to remove the solid desiccant that was easily introduced through the narrow neck of the upper portion 921, encouraging single use and disposal of the used mist generator, thus avoiding release of contaminated material and disinfectant into the hospital environment.

Flexible hoses (fixed or detached) from the outlet flow port of the mist generator to the inflow port of a blower that is non-closed circuit, creating a temporary closed circuit that allows internal sterilization. An aliquot of sterile water can be introduced after the sterilization takes place to remove residual disinfectant, and then removed by uptake into a sponge or descant.

FDA recommended "regular cleaning" of patient heating devices which can be achieved with the subject system without changing any other components. Preferably to avoid a port into the chamber 910 that could be opened for filling, a soft diaphragm 905 is provided through which fluids can be introduced with a needle and syringe (similar to medicine vials). The disinfecting liquid may be contained in a sealed prefilled capsale, which is perforated when pushed into the chamber 910, releasing the enclosed fluid. The heated air causes the fluid of capsule 902 to atomize within chamber 910, whereupon it continues traveling with the warm forced air as a mist or vapor through tubes to sterilize devices attached thereto. Fluids contemplated include chemicals compositions having relatively low boiling points or volatility so that the disinfectant vaporizes upon being heated by way of the warm air. Examples include alcohols such as ethanol etc. Embodiments of the capsule/cartridge are shown in FIGS. 9b-9d.

Figure 9B:
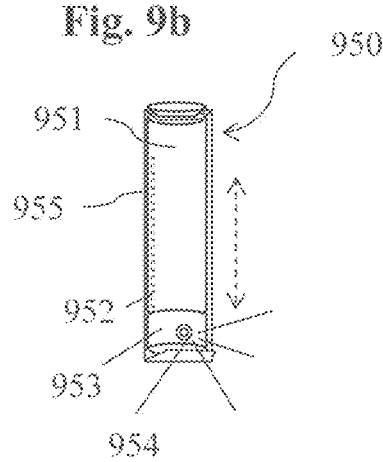

FIG. 9b illustrates another embodiment of a capsule/cartridge 950 adapted to be inserted within the mist generator of FIG. 9a. Capsule/cartridge 950 is a spray cartridge containing a liquid disinfectant/antimicrobial solution generally constructed as a spray bottle construction, including a reservoir 951 housing the liquid having a tube 952 therein. A cartridge pump 953 is provided with a trigger mechanism, a piston, a cylinder and a one-way valve in-line with a spray nozzle 954. Spray nozzle 954 includes a one-way valve to prevent air from flowing back into the pump and allowing suction within the pump so that liquid is pulled through tube 952. Nozzle 954 concentrates the liquid into a stream forcing it through a small hole. When the trigger is pressed, it forces the piston into the cylinder, which forces the liquid through the nozzle as a concentrated stream of liquid. When the trigger is released, the piston moves back, pulling liquid back into the cylinder. This liquid is forced out of the nozzle the next time the trigger is pressed. A one-way valve at the bottom of the pump only allows liquid to flow up the tube into the pump, not back into the bottle. The mist generator preferably includes a spray activator herein shown as a bracket 955 that the capsule/cartridge 950 sits within when it is inserted in the chamber of the mist generator. Bracket 955 may be provided so that it is in-line with a manual button that when depressed presses the capsule/cartridge 950 downward and causes the trigger of the pump to be activated to release spray. Preferably, bracket 955 is in-line with an electronic switch that activates the trigger to cause release of the spray.

Figure 9C:
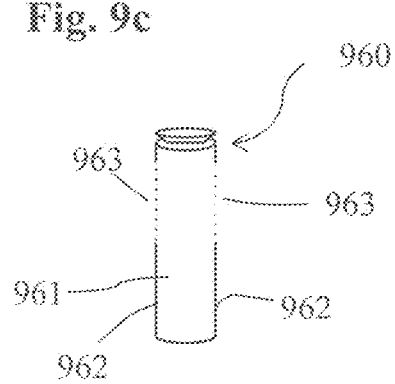
Figure 9D:
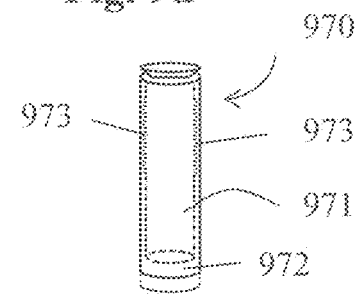

FIG. 9c illustrates an embodiment of a capsule/cartridge 960 adapted to be inserted within the mist generator of FIG. 9a. In this embodiment, capsule/cartridge 960 includes a reservoir 961 holding a volatile disinfectant liquid and side walls 962 having at least a portion therein that include small apertures or perforations 963 for release of misted liquid as air passes through the chamber of the mist generator. It is noted that the reservoir 961 may hold a volatile disinfectant liquid, or a semi solid or membrane holding the liquid that releases the liquid as forced heated air passes through the chamber of the mist generator.

Figure 10:
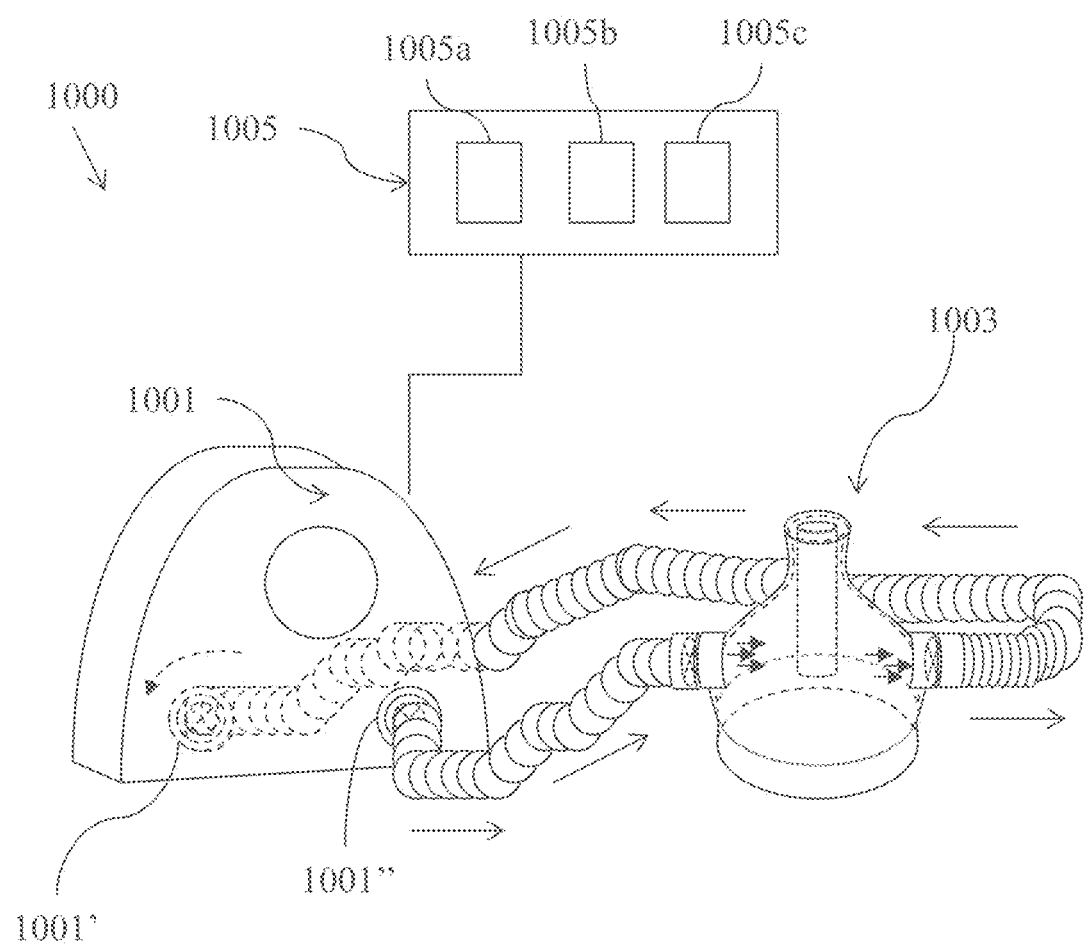
FIG. 10 illustrates the embodiment of FIG. 9 connected to a blower with air warmer machinery and flexible tubes being sterilized by the antimicrobial/disinfectant mist generator.

A separate capsule/cartridge may be provided housing a fiber or desiccant when the mist generator is in a drying mode such as after the disinfectant procedure is complete. The user simply places a capsule/cartridge housing the disinfectant into the chamber of the mist generator and runs a disinfectant operation for a period of time as shown in FIG. 10. When the disinfectant run is complete, the user can simply remove the capsule/cartridge and replace it with a drying capsule/cartridge that contains fiber or desiccant and performs a drying run for a period of time to dry liquid/residual mist from the generator, tubes and blower. Upon completion, the capsules/cartridges, as well as the mist generator itself, are preferably discarded.

FIG. 9d illustrates another embodiment of a capsule/cartridge 970 adapted to be inserted within the mist generator of FIG. 9a. In this embodiment, the reservoir 971 housing the disinfectant is located within a capsule chamber 972. At least a portion of side walls 973 of the reservoir has apertures or holes therein for the escape of misted disinfectant as air passes through the chamber of the mist generator.

FIG. 10 illustrates at 1000 another embodiment of the blower with air warmer machinery and flexible tubes being sterilized by the antimicrobial mist generator. The blower with air warmer machinery is shown at 1001 with HEPA filters both at inlet and outlet 1001' and 1001". The output 1001" of the blower 1001 is connected to the inlet of the antimicrobial mist generator 1003 using a flexible hose provided with quick release couplings. The output of the antimicrobial mist generator 1003 is connected to the inlet port 1001' of the blower 1001 using a flexible hose provided with quick release couplings temporarily forming a closed circuit system. The antimicrobial solution in the antimicrobial mist generator is atomized and circulated in this closed path for a preselected time period, which may be as long as 15 minutes, disinfecting circuit sterilizing the blower with air warming machinery 1001 and all the flexible hoses in the system. At the end of this disinfecting step, any moisture present in the blower 1001 and flexible hoses is taken up into a dry sponge. The quick release couplings are then disconnected.

The microprocessor control panel is shown at 1005. The microprocessor controls the warm air temperature at 1005*a* warm airflow rate at 1005*b* and warm air pressure at 1005*c*. The warm airflow path is therefore a continuous closed circuit with no warm air escape location. The airflow rate is proportional to the speed of rotation of the blower motor. The electrical current supplied to the heating elements controls the warm air temperature.

Figure 11:
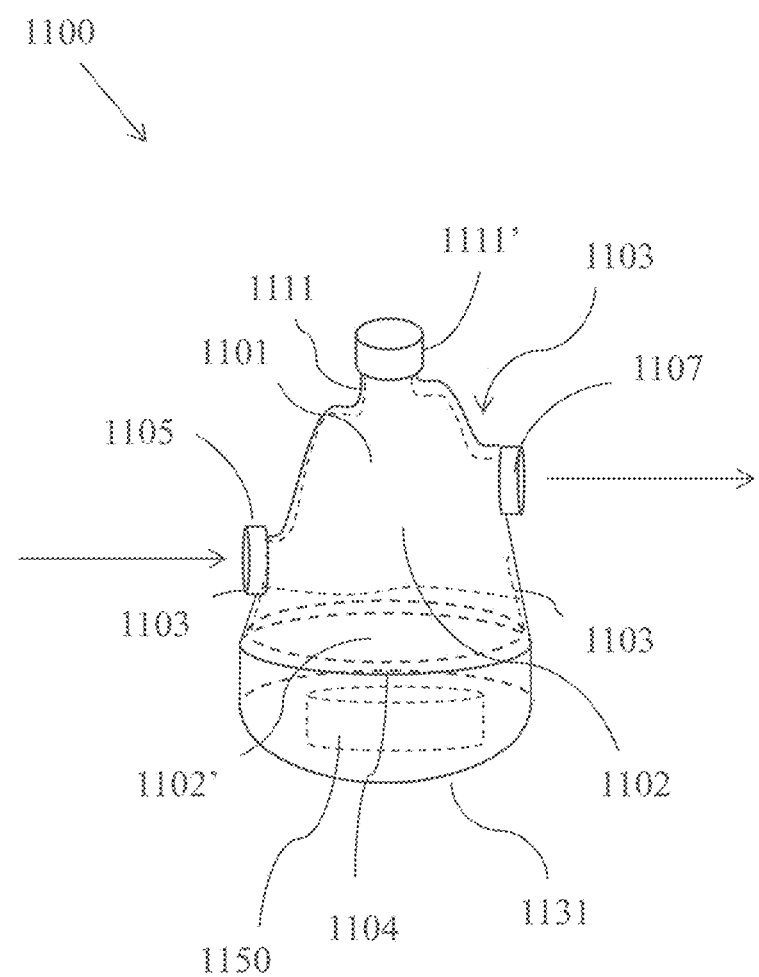
FIG. 11 illustrates another embodiment of the antimicrobial mist generator.

FIG. 11 illustrates another embodiment of the subject mist generator, shown generally at 1100. The mist generator comprises a main body 1101 having a top wall 1111 with an opening 1111', the opening traversing into a chamber 1102 adapted to receive a disinfectant shown generally at 1102', side walls 1103 and a bottom wall 1104. The main body 1101 further includes an inlet duct 1105 adapted for attachment to a first hose which in turn is adapted for attachment to an output opening of a blower for delivery of forced air into the chamber 1102 to create misted disinfectant in the air. The main body 1101 also includes an output duct 1107 adapted for attachment to a second hose which in turn is adapted for attachment to a blower inlet opening of the blower for delivery of disinfectant misted air through internal components of the blower. In the embodiment shown, the bottom wall 1104 includes a bottom opening with a removable bottom cover 1131, which can cause removal of the main body 1101 from bottom cover 1131 for insertion of desiccant, and/or paper towels, etc. In the embodiment shown, cover 1131 also includes an optional transducer 1150 for vibration misting the liquid within the chamber.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A mist generator for improved sterility of blowers having controlled forced air delivery, consisting of:

a) a main body having a top wall with an opening, the opening traversing into a chamber adapted to receive a disinfectant, side walls and a bottom wall;

b) an inlet duct adapted for attachment to a first hose which in turn is adapted for attachment to an output opening of a blower for delivery of forced air into the chamber to carry disinfectant misted air;

c) an output duct adapted for attachment to a second hose which in turn is adapted for attachment to a blower inlet opening of the blower for delivery of disinfectant misted air through internal components of the blower;

whereby the mist generator improves sterility of the blower to mitigate microbial contamination of patient warmers and lifters and hospital environments.

2. The mist generator as recited by claim 1, wherein the blower is part of a non-closed circuit and said first and second hoses have quick release couplings configured to be disconnected from said mist generator and connected to a patient warmer.

3. The mist generator as recited by claim 1, wherein the blower has microprocessor controlled air heating capability for delivery of heated forced air, and said disinfectant is adapted to evaporate due to the heated forced air to yield misted air containing disinfectant.

4. The mist generator as recited by claim 3, wherein said disinfectant is a volatile liquid component that is adapted to vaporize as forced air blows over said disinfectant.

5. The mist generator as recited by claim 3, wherein said disinfectant is a volatile liquid component saturated within a substrate and said liquid vaporizes and escapes said substrate as forced air blows over said substrate.

6. The mist generator as recited by claim 1 comprising a transducer facilitating formation of said disinfectant mist.

7. The mist generator as recited by claim 1, wherein said disinfectant is an aqueous solution.

8. The mist generator as recited by claim 1, wherein said disinfectant is an alcohol solution.

9. The mist generator as recited by claim 1 comprising a sterilization cycle set to run for a preselected time period.

10. The mist generator as recited by claim 1, wherein said mist generator is disposable.

11. The mist generator as recited by claim 1, wherein the inlet duct and the output duct are located on opposite side walls.

12. The mist generator as recited by claim 1, wherein the bottom wall includes a bottom opening with a removable bottom cover.

13. The mist generator as recited by claim 1 comprising a microprocessor for controlling the amount of disinfectant delivered for atomization into the chamber of the mist generator.

14. The mist generator as recited by claim 1, comprising a soft diaphragm located on said opening of said top wall through which fluids are to be introduced with a syringe needle.

15. The mist generator as recited by claim 1 wherein said disinfectant is contained in a capsule adapted to be inserted within said chamber of said mist generator.

16. The mist generator as recited by claim 15, wherein said disinfectant is a liquid and said capsule is a spray capsule, wherein said chamber of said mist generator includes a spray activator for release of said disinfectant as a spray within said chamber of said mist generator.

17. An improvement in sterilizing non-closed circuit patient warmers, the improvement consisting of a mist generator containing a disinfectant constructed having an inlet duct traversing to a chamber containing the disinfectant; an output duct adapted for attachment to a second hose which in turn is adapted for attachment to a blower inlet opening of the blower and an output duct from said chamber, allowing for delivery of disinfectant misted air through internal components of the blower, the inlet opening of the blower and the output duct from the chamber, together with a first hose connected to and in communication with a blower outlet opening and said inlet duct of said chamber, adapted to form a closed circuit and run a sterilization cycle for a preselected time period.

18. The improvement as recited by claim 17, wherein said preselected time period is less than 15 minutes.

19. The improvement as recited by claim 17, wherein the mist generator comprises a soft diaphragm through which fluids are to be introduced with a syringe needle.

* * * * *